US006426100B2

(12) United States Patent
Watkins et al.

(10) Patent No.: US 6,426,100 B2
(45) Date of Patent: Jul. 30, 2002

(54) METHOD FOR IMPROVING BONE MODELING AND CHONDROCYTE FUNCTIONING IN GROWING CANINES

(75) Inventors: Bruce A. Watkins, West Lafayette, IN (US); Allan J. Lepine, Lewisburg, OH (US); Michael G. Hayek; Gregory A. Reinhart, both of Dayton, OH (US)

(73) Assignee: The Iams Company, Dayton, OH (US)

( * ) Notice: Subject to any disclaimer, the term of this patent is extended or adjusted under 35 U.S.C. 154(b) by 0 days.

(21) Appl. No.: 09/785,901

(22) Filed: Feb. 16, 2001

Related U.S. Application Data

(60) Provisional application No. 60/183,294, filed on Feb. 17, 2000.

(51) Int. Cl.$^7$ ................................................. A23K 1/18
(52) U.S. Cl. ......................... 426/2; 426/601; 426/805
(58) Field of Search ............................ 426/2, 601, 805

(56) References Cited

U.S. PATENT DOCUMENTS

| | | | | |
|---|---|---|---|---|
| 5,069,903 A | 12/1991 | Stitt | ........................ | 424/195.1 |
| 5,585,117 A | 12/1996 | Dietz | ........................ | 424/693 |

FOREIGN PATENT DOCUMENTS

| | | |
|---|---|---|
| CA | 2145716 | 11/1998 |
| EP | 0585026 | 3/1994 |
| JP | 01157912 | 6/1989 |
| JP | 253908 | 9/1992 |
| JP | 06092847 | 4/1994 |
| JP | 10127257 | 5/1998 |
| WO | WO 96/31457 | 10/1996 |
| WO | WO 99/53969 | 10/1999 |

OTHER PUBLICATIONS

Weiler, H. et al., Abstract, "Supplemental Arachidonic (AA) and Docosahexaenoic (DHA) Acids Increase Bone Mineral Density, but not Calcium Absorption, in Piglets," Pediatric Research, Neonatal Nutrition & Metabolism, 1998, 1586, p. 271A.

Watkins, B. et al., "Importance of Dietary Fat in Modulating $PGF_2$ Responses and Influence of Vitamin E on Bone Morphometry," Nutrition and Fitness: Metabolic and Behavioral Aspects in Health and Disease. World Rev Nutr Diet. Basel, Karger, 1997, vol. 82, pp. 250–259.

Seifert, M. et al., "Role of Dietary Lipid and Antioxidants in Bone Metabolism," Nutrition Research, 1997, vol. 17, No. 7, pp. 1209–1228.

Reeves, P. et al., Committee Report, "AIN–93 Purified Diets for Laboratory Rodents: Final Report of the American Institute of Nutrition Ad Hoc Writing Committee on the Reformulation of the AIN–76A Rodent Diet," American Institute of Nutrition, 1993, pp. 1939–1951.

Cathcart, E. et al., "Fish Oil Fatty Acids and Experimental Arthritis," Nutrition and Rheumatic Diseases, vol. 17, No. 2, May 1991, pp. 235–242.

Claassen, N. et al., "Supplemented Gamma–Linolenic Acid and Eicosapentaenoic Acid Influence Bone Status in Young Male Rats: Effects on Free Urinary Collagen Crosslinks, Total Urinary Hydroxyproline, and Bone Calcium Content," Bone, vol. 16, No. 4, Supplement, Apr. 1995, pp. 385S–292S.

Kruger, M. et al., "Calcium, gamma–linolenic acid and eicosapentaenoic acid supplementation in senile osteoporsis," Aging Clin. Exp. Res., vol. 10, No. 5, 1998, pp. 385–394.

Kruger, M. et al., "Correlation between essential fatty acids and parameters of bone formation and degradation," Asia Pacific J. Clin Nutr, 1997, 6, pp. 235–238.

Venkatraman, J. et al., "Effects of Dietary w–3 and w–6 Lipids and Vitamin E on Serum Cytokines, Lipid Mediators and Anti–DNA Antibodies in a Mouse Model for Rheumatoid Arthritis," Journal of the American College of Nutrition, vol. 18, No. 6, 1999, pp. 602–613.

Van Papendorp, D. et al., "Biochemical Profile of Osteoporotic Patients on Essential Fatty Acid Supplementation," Nutrition Research, vol. 15, No. 3, 1995, pp. 325–334.

Kruger, M. et al., Abstracts—The 25th European Symposium on Calcified Tissues, Essential Fatty Acids, Calcium Homeostasis and Bone Turnover, Bone, Apr. 1997, vol. 20, No. 4S, S017.

Horrobin, Abstracts—The 25th European Symposium on Calcified Tissues, "Essentials Fatty Acid Metabolism and Bone," Bone, 1997, vol. 20, No. 4S, S015.

Claassen, H. et al., "The Effect of Different n–6/n–3 Essential Fatty Acid Ratios on Calcium Balance and Bone in Rats," Prostaglandins Leukotrienes and Essential Fatty Acids, 1995, 53, pp. 13–19.

Johanson J. et al., Abstract, "Bone Phospholipid Fatty Acids and Bone Ash Differed in Piglets Fed Diets Containing Eicosapentaenoic or Linoleic Acid for 12 Days," The FASEB Journal, Mar. 17, 1998, vol. 12, No. 4, p. A231.

DAS, Forum "Can essential fatty acids prevent osteoporosis?" Med. Sci. Res., 1994, 22, pp. 163–165.

(List continued on next page.)

*Primary Examiner*—Chhaya D. Sayala
(74) *Attorney, Agent, or Firm*—Schwegman, Lundberg, Woessner & Kluth, P.A.

(57) ABSTRACT

A process is provided for promoting bone modeling and chondrocyte functioning in growing canines. The process includes administering to a growing canine a pet food composition which includes an appropriate amount and ratio of dietary n-6 and n-3 fatty acids. The composition can further include a source of protein, a source of fat, a source of fiber, and a source of carbohydrates. Use of the preferred concentrations of n-6 and n-3 fatty acids can promote synthesis and tissue accumulation of down regulating elements of inflamation, which stimulate bone formation and optimize bone modeling.

17 Claims, No Drawings

OTHER PUBLICATIONS

Raisz, L., "Bone Cell Biology: New Approaches and Unanswered Questions," Journal of Bone and Mineral Research, vol. 8, Supplement 2, 1993, pp. S457–S465.

Watkins, B. et al., "Food Lipids and Bone Health," Marcel Dekker,Inc., pp. 71–116, Jun. 96.

Adkisson, IV, H. et al., "Unique fatty acid composition of normal cartilage: discovery of high levels of n–9 eicosatrienoic acid and low levels of n–6 polyunsaturated fatty acids," FASEB, 1991, pp. 344–353.

Xu, H. et al., "Dietary Lipids Modify the Fatty Acid Composition of Cartilage, Isolated Chondrocytes and Matrix Vesicles," Lipids, vol. 29, No. 9, 1994, pp. 619–625.

Watkins, B. et al., Biochemical and Molecular Roles of Nutrients, "Dietary Lipids Modulate Bone Prostaglandin $E_2$ Production, Insulin–Like Growth Factor–I Concentration and Formation Rate in Chicks," American Society for Nutritional Sciences, 1997, pp. 1084–1091.

Li, Y. et al., "Conjugated Linoleic Acids Alter Bone Fatty Acid Composition and Reduce ex vivo Prostaglandin $E_2$ Biosynthesis in Rats Fed n–6 or n–3 Fatty Acids," Lipids, vol. 33, No. 4, 1998, pp. 417–425.

Watkins, B. et al., "Dietary (n–3) and (n–6) Polyunsaturates and Acetylsalicyclic Acid Alter Ex Vivo $PGE_2$ Biosynthesis, Tissue IGF–I Levels, and Bone Morphometry in Chicks," Journal of Bone and Mineral Research, vol. 11, No. 9, 1996, pp. 1321–1332.

Norrdin, R. et al., "The Role of Prostaglandins in Bone in vivo," Prostaglandins Leukotrienes and Essential Fatty Acids, 1990, pp. 193–149.

Xu, H. et al., "Vitamin E Stimulates Trabecular Bone Formation and Alters Epiphyseal Cartilage Morphometry," Calcif Tissue Int, 57, 1995, pp. 293–300.

Watkins, B. et al., "Linoleate Impairs Collagen Synthesis in Primary Cultures of Avian Chondrocytes," Fatty Acids and Chondrocyte Function, 1996, pp. 153–159.

Raisz, L. et al., "Effects of Prostaglandin E and Eicosapentaenoic Acid on Rat Bone in Organ Culture," Prostaglandins, May 1989, vol. 37, No. 5, pp. 615–625.

METHOD FOR IMPROVING BONE MODELING AND CHONDROCYTE FUNCTIONING IN GROWING CANINES

This application claims the benefit of U.S. Provisional application No. 60/183,294, filed Feb. 17, 2000.

BACKGROUND OF THE INVENTION

The present invention relates to a process of administering to growing canines a pet food composition comprising appropriate amounts and ratios of n-6/n-3 fatty acids to enhance bone modeling and chondrocyte functioning in those animals.

It is known from Canadian Patent No. 2,145,716 that dietary n-6 and n-3 fatty acids (also known as omega-6 and omega-3 fatty acids) and the ratio in which they are present in the canine diet has an effect on the skin and coat health of the animal. Studies have demonstrated that the incorporation of optimal proportions of n-6 and n-3 fatty acids into the diet has a beneficial effect on canines suffering from certain inflammatory skin conditions.

Long bone growth and bone modeling are regulated by complex interactions between a puppy's genetic potential, environmental influences, and nutrition. These interactions produce a bone architecture that balances functionally appropriate morphology with the skeleton's role in calcium and phosphorous homeostasis. Long bones of the dog increase in length and diameter by a process called modeling. Bone modeling represents an adaptive process of generalized and continuous growth and reshaping of bone governed by the activities of osteoblasts and osteoclasts until the adult bone structure is attained. Bone modeling is distinct from bone remodeling which describes the process of bone resorption and formation that maintains skeletal mass in the adult dog.

There are numerous cell-derived growth regulatory factors present within skeletal tissues such as prostaglandins, cytokines, and growth factors which affect skeletal metabolism. Prostaglandins are believed to play a major role in bone metabolism, but also have been implicated in joint diseases. Some of the skeletal abnormalities and conditions in canines are the consequence of abnormal bone remodeling and metabolism, or in the case of arthritis, an inflammatory process.

Growth cartilage in long bones contains chondrocytes which initiate bone mineralization through matrix vesicles which have been described as lipid-enclosed microenvironments containing acidic phospholipids that exhibit a high affinity for binding calcium ions. Polyunsaturated fatty acids (PUFA) are believed to play an important role in bone mineralization and growth because it is believed that phospholipids as well as prostaglandins are synthesized from essential PUFA.

Recent studies have demonstrated that dietary n-6/n-3 fatty acids ratios are reflected in the fatty acid profile in the bones and growth cartilage of growing chicks and in the bones of rats. In these studies, chicks provided with soybean oil in their diet had greater values for ex vivo $PGE_2$ (prostaglandin $E_2$) production in liver and bone cultures, but lower bone formation rates as compared to chicks fed menhaden oil. The level of $PGE_2$ produced locally at the bone appears to be a critical factor in bone formation in that it is stimulatory at moderate levels and inhibitory at high levels. The mechanism by which prostaglandins regulate bone metabolism is uncertain but it has been suggested that it may be mediated through the IGF system and(or) cytokines.

Accordingly, the need remains in the art for a diet which promotes bone/cartilage biology and health in the growing canine, which diet includes appropriate amounts of dietary n-6 and n-3 fatty acids.

SUMMARY OF THE INVENTION

The present invention meets that need by providing a process of administering to a growing canine a pet food composition comprising an appropriate amount and ratio of dietary n-6 and n-3 fatty acids to provide improved bone modeling and chondrocyte functioning. In accordance with one aspect of the present invention, a process is provided for improving bone modeling and chondrocyte functioning in a growing canine comprising the step of feeding the growing canine a pet food composition comprising n-6 and n-3 fatty acids in an amount and ratio effective to improve bone modeling and chondrocyte functioning. The ratio of n-6 fatty acids to n-3 fatty acids is preferably from about 20:1 to about 1:1, more preferably, from about 10:1 to about 5:1, and most preferably, from about 8:1 to about 5:1. It is preferred that at least about 22 wt% of the total fatty acids in the pet food composition are n-6 fatty acids. It is also preferred that at least about 3 wt% of the total fatty acids in the pet food composition are n-3 fatty acids.

Preferably, the pet food composition comprises from about 0.88 to about 6.6% by weight n-6 fatty acids and from about 0.16 to about 1.2% by weight n-3 fatty acids, on a dry matter basis. Thus, both the amount of n-3 fatty acids in the pet food composition, as well as the ratio of n-6 to n-3 fatty acids, are important. In a preferred embodiment, the n-3 fatty acids provided in the pet food composition comprise eicosapentaenoic acid (EPA) and docosahexaenoic acid (DHA).

Preferably, the pet food composition comprises from about 20 to about 40 wt% crude protein, from about 4 to about 30 wt% fat, from about 2 to about 20 wt% total dietary fiber, and a source of carbohydrates. No specific ratios or percentages of these nutrients are required.

The pet food composition may further comprise from about 1 to about 11 weight percent of supplemental total dietary fiber of fermentable fibers which have an organic matter disappearance of 15 to 60 weight percent when fermented by fecal bacteria for a 24 hour period.

Accordingly, it is a feature of the present invention to provide a process for improving bone modeling and chondrocyte functioning in a growing canine. This, and other features and advantages of the present invention will become apparent from the following detailed description and the appended claims.

DETAILED DESCRIPTION OF THE PREFERRED EMBODIMENT

The present invention utilizes a pet food composition which aids in promoting bone development in growing canines by providing appropriate amounts of n-6 and n-3 fatty acids, and in proper ratios, to stimulate chondrocyte functioning and bone development. The pet food composition may be provided in any suitable form as long as it contains the preferred concentrations of n-3 and n-6 fatty acids.

In adult canines, abnormal bone remodeling and metabolism can cause skeletal pathologies. Feeding the pet food composition of the present invention to growing canines early in life may delay or lessen the onset and severity of some of these pathologies. Therefore, growing canines will especially benefit from being fed the pet food composition of the present invention.

It has been discovered that by adjusting the ratio of n-6 to n-3 fatty acids in the pet food composition, the level of certain pro-inflammatory eicosanoid prostaglandins ($PGE_2$) are depressed. In accordance with the preferred embodiment of the present invention, the pet food composition comprises a ratio of n-6 fatty acids to n-3 fatty acids that is from about 20:1 to about 1:1. More preferably, this weight ratio is from about 10:1 to about 5:1. Most preferably, this weight ratio is from about 8:1 to about 5:1. Preferably, at least about 22 wt% of the total fatty acids in the pet food composition are n-6 fatty acids. It is also preferred that at least about 3 wt% of the total fatty acids in the pet food composition are n-3 fatty acids. The pet food composition also preferably comprises from about 0.88 to about 6.6% by weight n-6 fatty acids and from about 0.16 to about 1.2% by weight n-3 fatty acids, on a dry matter basis.

Synthesis and tissue accumulation of down regulating elements of inflammation such as the n-3 fatty acids eicosapentaenoic and docosahexaenoic acids (EPA and DHA, respectively) are also promoted by adjusting the ratio of n-6 to n-3 fatty acids in the pet food composition of the present invention, which stimulates bone formation and optimizes bone modeling. Further, by providing specific sources of n-3 fatty acids to the pet food composition, tissue accumulation of anti-inflammatory $PGE_3$ series prostaglandins is promoted as well. Preferably, the n-3 fatty acids of the pet food composition of the present invention comprise EPA and DHA.

The pet food composition can be any suitable pet food formula that also provides adequate nutrition for the animal. For example, a typical canine diet for use in the present invention may contain from about 20 to about 40 wt% crude protein, from about 4 to about 30 wt% fat, and from about 2 to about 20 wt% total dietary fiber, along with a source of carbohydrates. Suitable sources of protein for use in the pet food composition include, but are not limited to, chicken and chicken-by-products, chicken digest, brewers dried yeast, and DL-methionine. Suitable sources of fat include chicken fat (preserved with mixed tocopherols), fish oil, and flax.

The pet food composition of the present invention may also optionally contain a source of fermentable fibers that display certain organic matter disappearance percentages. The fermentable fibers that may be used have an organic matter disappearance (OMD) of from about 15 to 60 percent when fermented by fecal bacteria in vitro for a 24 hour period. That is, from about 15 to 60 percent of the total organic matter originally present is fermented and converted by the fecal bacteria. The organic matter disappearance of the fibers is preferably 20 to 50 percent, and most preferably is 30 to 40 percent.

Thus, in vitro OMD percentage may be calculated as follows:

$$\{1-[(OM\ residue - OM\ blank)/OM\ initial]\} \times 100,$$

where OM residue is the organic matter recovered after 24 hours of fermentation, OM blank is the organic matter recovered in corresponding blank tubes (i.e., tubes containing medium and diluted feces, but no substrate), and OM initial is that organic matter placed into the tube prior to fermentation. Additional details of the procedure are found in Sunvold et al., J. Anim. Sci. 1995, vol. 73:1099–1109.

The fermentable fibers may be any fiber source that intestinal bacteria present in the animal can ferment to produce significant quantities of short chain fatty acids (SCFAs). "Significant quantities" of SCFAs, for purposes of this invention, are amounts over 0.5 mmol of total SCFAs/gram of substrate in a 24-hour period. Preferred fibers include beet pulp, gum arabic (including gum talha), psyllium, rice bran, carob bean gum, citrus pulp, pectin, fructooligosaccharids and inulin, mannanoligosaccharides and mixtures of these fibers.

The fermentable fibers are used in the pet food composition in amounts from 1 to 11 weight percent of supplemental total dietary fiber, preferably from 2 to 9 weight percent, more preferably from 3 to 7 weight percent, and most preferably from 4 to 7 weight percent.

A definition of "supplemental total dietary fiber" first requires an explanation of "total dietary fiber". "Total dietary fiber" is defined as the residue of plant food which is resistant to hydrolysis by animal digestive enzymes. The main components of total dietary fiber are cellulose, hemicellulose, pectin, lignin, and gums (as opposed to "crude fiber", which only contains some forms of cellulose and lignin). "Supplemental total dietary fiber" is that dietary fiber which is added to a food product above and beyond any dietary fiber naturally present in other components of the food product. Also, a "fiber source" is considered such when it consists predominantly of fiber.

In order that the invention may be more readily understood, reference is made to the following examples, which are intended to be illustrative of the invention, but are not intended to be limiting in scope.

EXAMPLE 1

A canine study evaluated the dietary n-3 and n-6 fatty acid effects on the fatty acid composition of bone compartments in coonhounds. A total of 32 eight-week-old purpose-bred puppies were allocated to four dietary treatments differing only in fatty acid source. Treatment diets were isonitrogenous, isocaloric and formulated to provide n-6/n-3 ratios ranging from 5:1 to 50:1. The canine growth diet was formulated to contain different ratios of n-6/n-3 fatty acids, 5:1, 5:1, 50:1, and 25:1, using the following lipid sources: docosahexaenoic acid (DHA), menhaden oil (MEN), safflower oil (SAF) and poultry fat (control). Treatments 3 and 4 evaluated the effect of n-3 fatty acid source (Treatment 3 =DHA; Treatment 4=DNA). Puppies were fed the treatment diets for a total of 18 weeks, 2 of weeks conditioning followed by 16 weeks of treatment. The results of the study are reported below.

| Treatment No. | Fat Source | n-6/n-3 Ratio* |
| --- | --- | --- |
| 1 | Poultry Fat | 25:1 |
| 2 | Safflower Oil | 50:1 |
| 3 | Menhaden Oil | 5:1 |
| 4 | DHA Source | 5:1 |

*Reported ratio is of the Fat Source.

The response criteria evaluated was as follows:

| Days on Test | Response Criteria |
| --- | --- |
| 0 | Serum TNF, IL-1 and IL-6. |
| 4 | Serum TNF, IL-1 and IL-6. |

| Days on Test | Response Criteria |
|---|---|
| 8 | Serum TNF, IL-1, IL-6, lipids, osteocalcin, alkaline phosphatase and IGF-1. |
| 12 | Serum TNF, IL-1 and IL-6. |
| 16 | Serum TNF, IL-1, IL-6, lipids, osteocalcin, alkaline phosphatase and IGF-1. Bone (Ileum) formation rate, histomorphometry, fatty acids. |

MEN and DNA diets elicited significant elevations in 22:6n-3 (DHA) relative to the control diet in neutral and polar lipids of tibia cortical and trabecular bone, marrow and periosteum. The MEN diet resulted in a significantly higher concentration of 20:5n-3 (EPA) in both lipid fractions of all tissues. The concentration of 18:2n-6 (linoleic acid) was significantly higher in both lipid fractions of all tissues except marrow polar lipids of those given the SAF diet. The MEN and DHA diets depressed 18:2n-6 in the polar lipid fractions of trabecular bone and marrow. In the MEN and DHA enriched diets, arachidonic acid (AA; 20:4n-6) concentration was significantly depressed and 22:6n-3 elevated in the neutral lipid fraction of periosteum. Both the MEN and DHA diets reduced 18:2n-6 and increased n-3 fatty acids in ligaments compared to the values in dogs given control and SAF-containing diets.

These data showed that both EPA and DHA were enriched in bone compartments, and that DHA accumulated to a greater extent in cortical bone polar lipids than EPA. Based on ex vivo $PGE_2$ production in iliac crest tissue, the MEN diet tended to lower prostanoid formation. Moreover, the down-regulating elements of inflammation ($PGE_3$) are stimulated by the presence of EPA. These results suggest that diets rich in n-3 fatty acids reduce pro-inflammatory eicosanoid ($PGE_2$) synthesis and promote tissue accumulation of down-regulating elements of inflammation (EPA and DHA) in bone compartments of canines. These results also suggest that pro-inflammatory $PGE_2$ production will be elevated by a dietary n-6/n-3 fatty acid ratio of 25:1 or greater and thereby depress bone formation, while a ratio of 5:1 will lower the level of $PGE_2$ and thereby stimulate bone formation and optimize bone modeling in the growing canine. The specific n-3 fatty acid (20:5n-3 or 22:6n-3) in the diet may also differentially modulate effects on cartilage and bone metabolism in the growing canine.

EXAMPLE 2

A study using rats was performed. The study was needed due to the nature of the data to be collected and the impracticality of collecting such data from the growing canine. Data collected included (1) harvesting of organs and tissues, (2) determination of bone formation rates (BFR) and growth cartilage morphometry as a measure of bone modeling, and (3) evaluation of mechanical properties on intact bones.

A total of 40 weanling male Harlan Sprague-Dawley rats (21 days old) were allocated to four dietary treatments for 42 days. The control diet (Treatment 1) was AIN93G (diet as reported by Reeves et al, AIN-93 *Purified Diets for Laboratory Rodents*, 123 J. Nutrition 1939–51 (1993)) that contained soybean oil and an n-6/n-3 fatty acid ratio of 8:1. The other three treatment diets provided supplemental fatty acids to mirror the n-6/n-3 fatty acid ratios of the canine experiment as closely as possible. The control diet contained 70 g/kg of added fat. The other three treatment diets were formulated with lipids to provide the following ratios of (n-6)/(n-3) fatty acids: 8:1 (soybean oil (SBO)), 50:1 (safflower oil (SAF)), 5:1 (docosahexaenoic acid (DHA)), and 5:1 (Menhaden oil (MEN)). Treatment diets are summarized in the following table:

| Treatment No. | Fat Source | n-6/n-3 Ratio* |
|---|---|---|
| 1 | Soybean oil | 8:1 |
| 2 | Safflower Oil | 50:1 |
| 3 | Menhaden Oil | 5:1 |
| 4 | DHA Source | 5:1 |

*Reported ratio is of the Fat Source.

The response criteria evaluated was as follows:

| Days on Test | Response Criteria |
|---|---|
| 21 | Serum IGF-1, BP-3, osteocalcin and alkaline phosphatase. |
| 42 | Serum IGF-1, BP-3, osteocalcin, alkaline phosphatase and fatty acids. Bone histomorphometric measurements on growth plate cartilage and trabecular bone. Bone fatty acids, $PGE_2$ and IGF-1. Tibia and femur mechanical properties. |

The MEN and DHA diets significantly elevated the concentrations of 20:5n-3 (EPA) and 22:6n-3 (DHA) in tibia cortical bone and marrow compared to the values in those given the SAF diet. The concentration of 20:4n-6 (AA) in bone compartments was unchanged by the dietary treatments. The DHA concentration in bone was lowest in rats given the SAF diet.

These data showed that both EPA and DHA were enriched in bone compartments, and that DHA accumulated to a greater extent in cortical bone polar lipids than EPA. Ex vivo $PGE_2$ production in the tibia was reduced in rats given the DHA diet compared to those on the SAF diet. Serum bone specific alkaline phosphatase was elevated in rats given the MEN diet compared to values in rats given the other diets. Total trabecular number and marrow area were higher in the DHA group compared with the SBO group; however, periosteal BFR was higher in those given the SBO and SAF diets. No differences were found between the dietary treatments for endosteal bone formation rates.

The results suggest that diets rich in n-3 fatty acids reduce pro-inflammatory eicosanoid ($PGE_2$) synthesis and promote tissue accumulation of down-regulating elements of inflammation (EPA and DHA) in bone compartments.

While certain representative embodiments and details have been shown for purposes of illustrating the invention, it will be apparent to those skilled in the art that various changes in the methods and apparatus disclosed herein may be made without departing from the scope of the invention, which is defined in the appended claims.

What is claimed is:

1. A process for improving bone modeling and chondrocyte functioning in a growing canine comprising the step of feeding said canine a pet food composition comprising a source of n-6 and n-3 fatty acids in amounts effective to improve bone modeling and chondrocyte functioning.

2. A process as claimed in claim 1 in which the ratio of n-6 fatty acids to n-3 fatty acids is from about 20:1 to about 1:1.

3. A process as claimed in claim 1 in which the ratio of n-6 fatty acids to n-3 fatty acids is from about 10:1 to about 5:1.

4. A process as claimed in claim 1 in which the ratio of n-6 fatty acids to n-3 fatty acids is from about 8:1 to about 5:1.

5. A process as claimed in claim 1 in which at least about 22 wt% of the total fatty acids in the pet food composition are n-6 fatty acids.

6. A process as claimed in claim 1 in which at least about 3 wt% of the total fatty acids in the pet food composition are n-3 fatty acids.

7. The process of claim 1 in which the pet food composition comprises from about 0.88 to about 6.6% by weight n-6 fatty acids and from about 0.16 to about 1.2% by weight n-3 fatty acids, on a dry matter basis.

8. The process of claim 1 in which the n-3 fatty acids of the pet food composition comprise eicosapentaenoic acid (EPA) and docosahexaenoic acid (DHA).

9. A process for improving bone modeling and chondrocyte functioning in a growing canine comprising the step of feeding said canine a pet food composition comprising from about 20 to about 40 wt% crude protein, from about 4 to about 30 wt% fat, from about 2 to about 20 wt% total dietary fiber, a source of carbohydrate, and a source of n-6 and n-3 fatty acids in amounts effective to improve bone modeling and chondrocyte functioning.

10. A process as claimed in claim 9 which further includes from about 1 to about 11 weight percent of supplemental total dietary fiber of fermentable fibers which have an organic matter disappearance of 15 to 60 weight percent when fermented by fecal bacteria for a 24 hour period.

11. A process as claimed in claim 9 in which the ratio of n-6 fatty acids to n-3 fatty acids is from about 20:1 to about 1:1.

12. A process as claimed in claim 9 in which the ratio of n-6 fatty acids to n-3 fatty acids is from about 10:1 to about 5:1.

13. A process as claimed in claim 9 in which the ratio of n-6 fatty acids to n-3 fatty acids is from about 8:1 to about 5:1.

14. A process as claimed in claim 9 in which at least about 22 wt% of the total fatty acids in the pet food composition are n-6 fatty acids.

15. A process as claimed in claim 9 in which at least about 3 wt% of the total fatty acids in the pet food composition are n-3 fatty acids.

16. The process of claim 9 in which the pet food composition comprises from about 0.88 to about 6.6% by weight n-6 fatty acids and from about 0.16 to about 1.2% by weight n-3 fatty acids, on a dry matter basis.

17. The process of claim 9 in which the n-3 fatty acids of the pet food composition comprise eicosapentaenoic acid (EPA) and docosahexaenoic acid (DHA).

* * * * *